United States Patent
Kingsley et al.

[11] Patent Number: 5,982,289
[45] Date of Patent: Nov. 9, 1999

[54] DRIP COUNTER APPARATUS

[75] Inventors: Robert B. Kingsley; Nathaniel E. Durnan, both of Yakima, Wash.

[73] Assignee: Dowty Aerospace Yakima, Yakima, Wash.

[21] Appl. No.: 09/160,966

[22] Filed: Sep. 25, 1998

[51] Int. Cl.⁶ .................................................. G08B 21/00
[52] U.S. Cl. .................... 340/609; 340/602; 340/606; 604/253
[58] Field of Search ..................... 340/602, 606, 340/609; 73/861.41; 250/574, 575, 577; 604/253

[56] References Cited

U.S. PATENT DOCUMENTS

| | | | |
|---|---|---|---|
| 3,596,515 | 8/1971 | Cramer | 73/861.41 |
| 3,994,423 | 11/1976 | Burg | 222/420 |
| 4,533,350 | 8/1985 | Danby et al. | 604/253 |
| 4,635,281 | 1/1987 | Jones | 377/21 |
| 4,673,820 | 6/1987 | Kamen | 250/573 |
| 4,680,977 | 7/1987 | Conero et al. | 73/861.41 |
| 4,718,896 | 1/1988 | Arndt et al. | 604/253 |
| 4,829,448 | 5/1989 | Balding et al. | 702/33 |
| 5,186,057 | 2/1993 | Everhart | 73/861.41 |
| 5,411,052 | 5/1995 | Murray | 137/392 |
| 5,703,568 | 12/1997 | Hegyi | 340/602 |

*Primary Examiner*—Jeffery A. Hofsass
*Assistant Examiner*—Van T. Trieu
*Attorney, Agent, or Firm*—William W. Haefliger

[57] ABSTRACT

In apparatus for counting a succession of falling liquid drops having teardrop shape, with a downwardly convex down side, the combination that includes a beam provider for providing a beam of electromagnetic radiation to sidewardly pass into the drop at its convex lower side, to be refracted within the drop to pass out of the drop at its convex lower side, and a beam detector located to detect the refracted beam that has passed sidewardly out of the drop at its convex lower side.

11 Claims, 3 Drawing Sheets

DRIP COUNTER APPARATUS

BACKGROUND OF THE INVENTION

This invention relates generally to counting or sensing of liquid drips, as for example is employed in determining the frequency of drop fall; and more particularly concerns improvements in instrumentation to accurately sense the falling of liquid drops.

Counting of falling drops is useful for many purposes. Among these are liquid flow rate determination, intravenous infusion systems, and others. There is need for enhanced reliability and accuracy of drip or drop counting, or drop fall sensing instrumentation.

SUMMARY OF THE INVENTION

It is a major object of the invention to provide improvements in drip or drop counting apparatus meeting the above need. Basically, apparatus is provided for counting a succession of falling liquid drops having teardrop shape, with a downwardly convex down side, the combination that includes a) a beam provider for providing a beam of electromagnetic radiation to sidewardly pass into the drop at its convex lower side, to be refracted within the drop to pass out of the drop at its convex lower side, b) and a beam detector located to detect the refracted beam that has passed sidewardly out of the drop at its convex lower side.

As will be seen, the falling drop typically has a maximum width zone, and the beam provider is located to direct the beam into the falling drop below that maximum width zone. Only the drop reduced diameter section is used for the needed refraction to bend the beam to impinge at the counter sensor. If beam refraction at the level of maximum drop width were employed, it would or could be erroneous, since that maximum width is also the diameter of continual flow, i.e. in the absence of drops. In this regard, the axes of beam travel into the drop, and out from the drop typically have predetermined angularity less than 90°, and related to the index of refraction of the liquid such that only that beam traveling through a section of the drop below its maximum width is counted. An infrared red beam is typically employed, although other frequency beams of electromagnetic orientation can be employed.

Yet another object is to provide drip counter apparatus having a drip supply conduit with a drip outlet located above the line of the beam passing into and out of the drop at predetermined angularity, below said maximum width zone of the falling drip.

An additional object is to provide a carrier body carrying said drop conduit, said body defining a slot in which said conduit is received, said body also carrying said beam provider and beam detector below the level of said conduit outlet. That body may advantageously have a downwardly extending drip passage in which the drip may freely fall in a zone defining a vertical axis, said beam provider and detector being located to respectively provide and receive the beam along respective axes directed toward said zone.

These and other objects and advantages of the invention, as well as the details of an illustrative embodiment, will be more fully understood from the following specification and drawings, in which:

DRAWING DESCRIPTION

DETAILED DESCRIPTION

Figure 1:
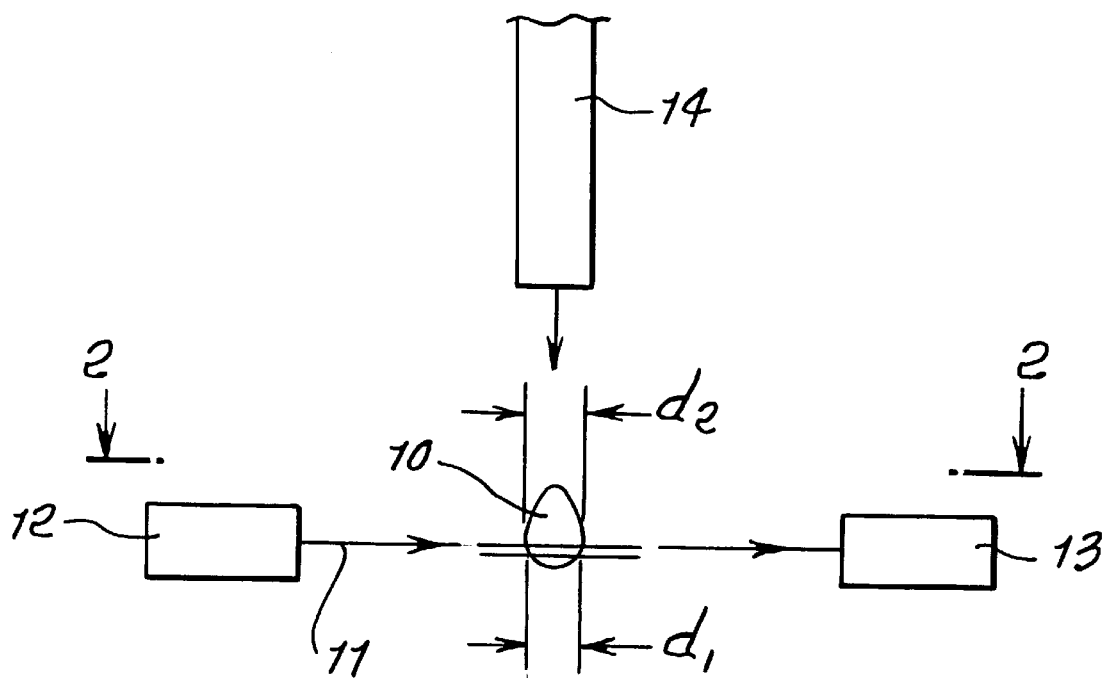
FIG. 1 is a schematic elevation showing a drip counter embodying the invention.
Figure 2:
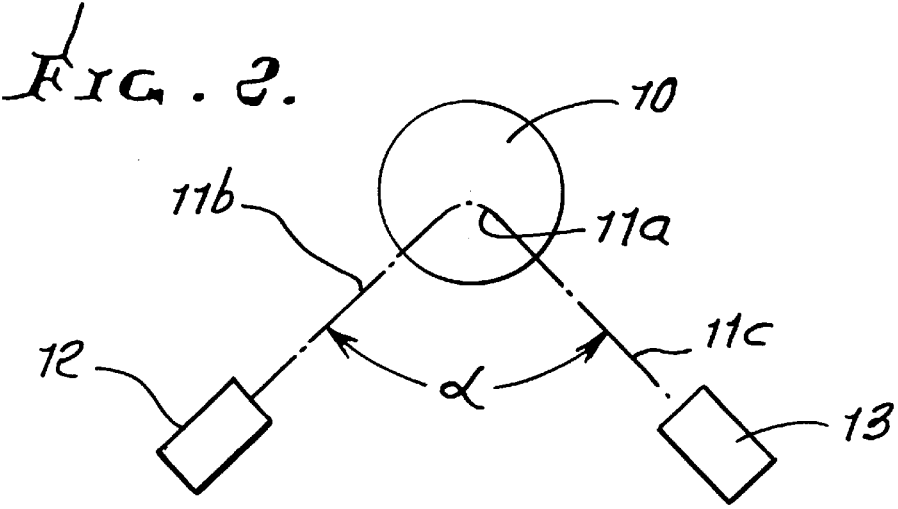
FIG. 2 is an enlarged plan view section, taken on lines 2—2 of FIG. 1.
Figure 3:
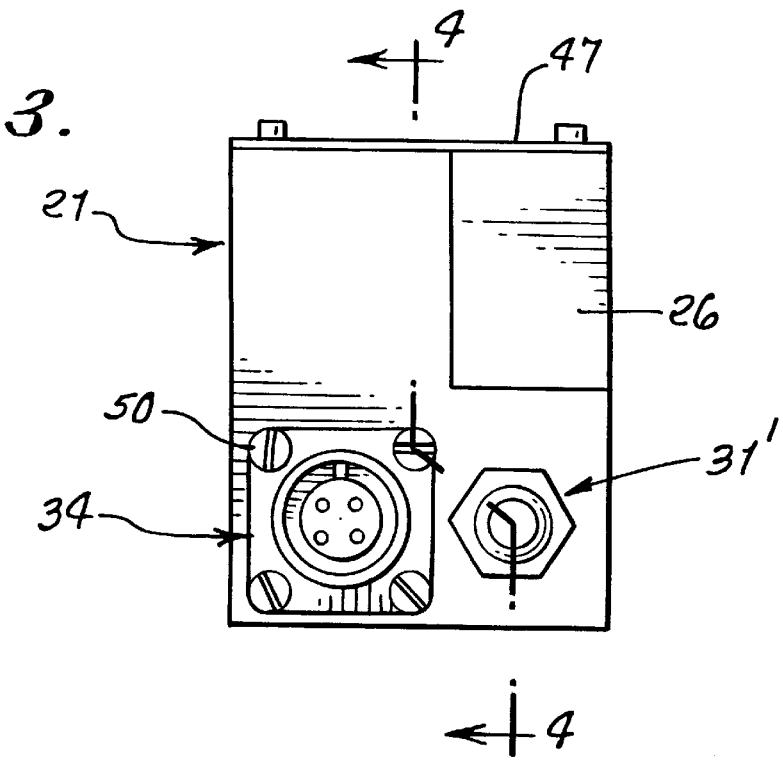
FIG. 3 is an elevation view of actual apparatus embodying the invention.
Figure 4:
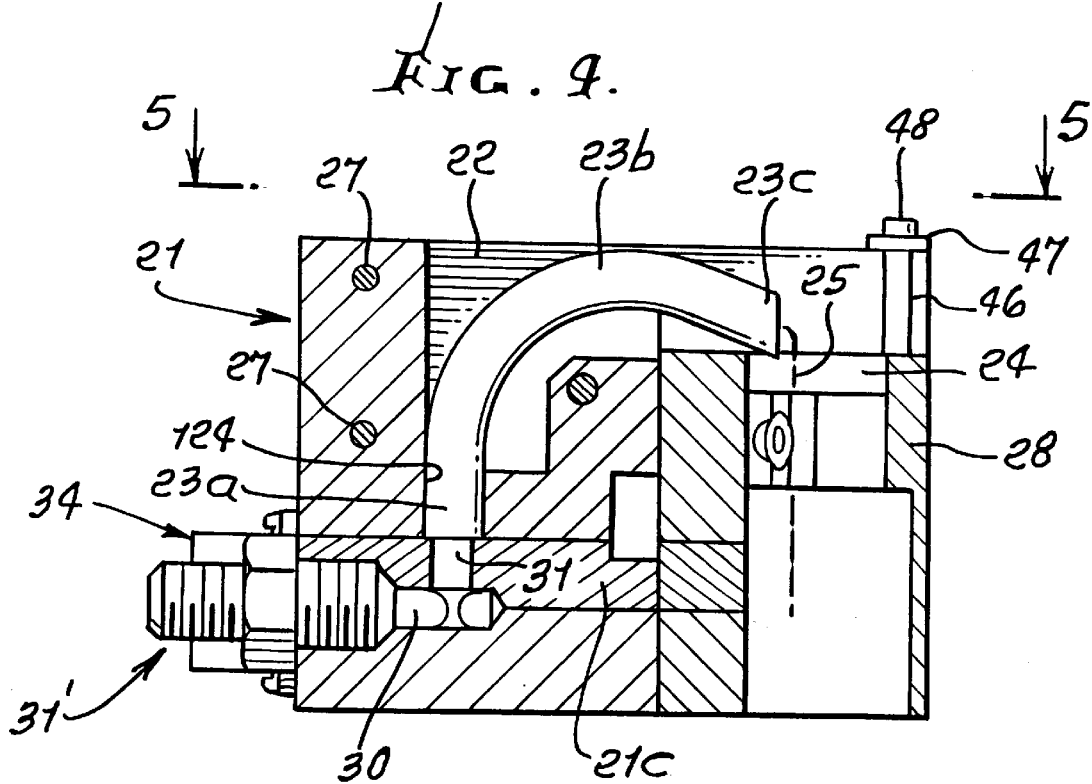
FIG. 4 is a section taken on lines 4—4 of FIG. 3.
Figure 5:
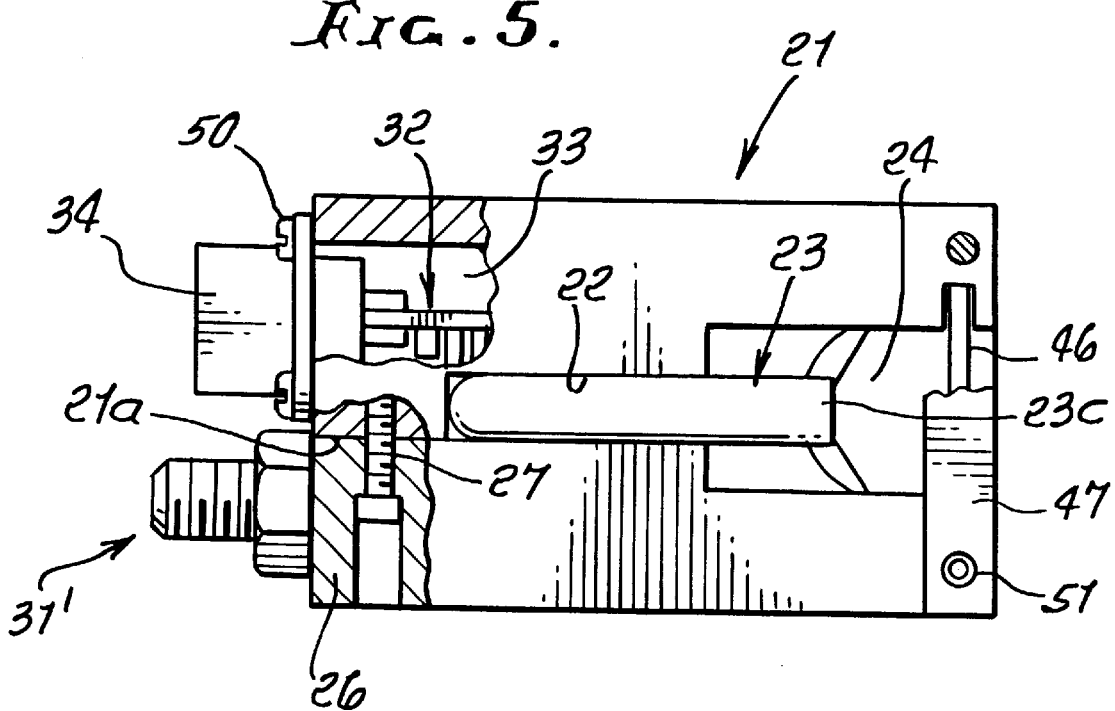
FIG. 5 is a plan view taken on lines 5—5 of FIG. 4.
Figure 6:
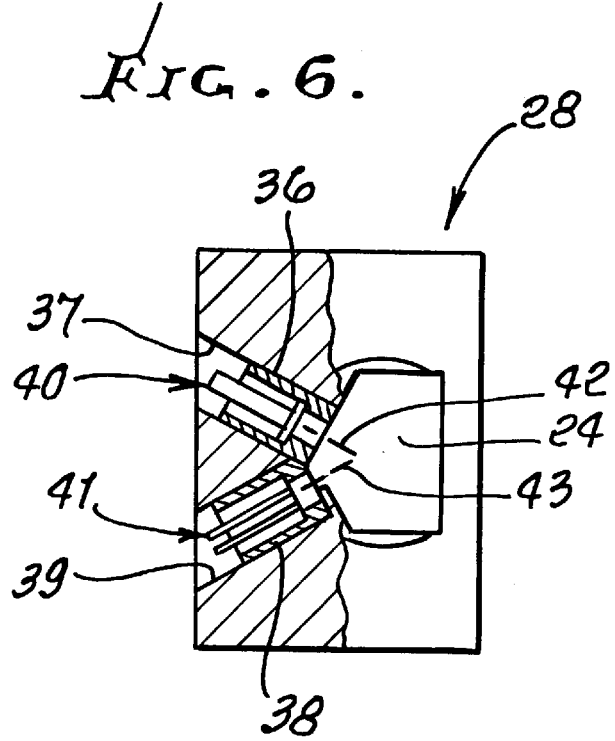
FIG. 6 is a horizontal section taken through a beam emitter and beam receiver, as used in the FIGS. 3–5 apparatus.

Referring first to FIGS. 1 and 2, a falling drop 10, such as an oil or water drop, is essentially transparent, to pass an electromagnetic beam 11 from a sensor 12 to a detector 13. The beam, which may be an infra-red light beam, is refracted, i.e. bent, as it passes through the falling drop. See refraction zone 11a in FIG. 2.

The dimensions including beam angularities, of axes at 11b and 11c, are such that only the drop reduced diameter $d_1$ is used for the needed refraction to bend the beam to impinge upon the detector. The major diameter $d_2$ of the falling drop is greater than $d_1$, i.e. the horizontal plane that contains $d_1$ is below the horizontal plane that contains $d_2$. Light refracted by regions of the drop outside the plane of $d_1$, does not pass along axis 11c, and so is not detected. Erroneous counting is thereby avoided.

Referring to FIGS. 3–6, a drip tube body 21 has a side recess 22 into which a drip tube 23 is received. The tube lower end 23a is pressed into a body slot 124, and sealed in position as by a Teflon retainer. The tube has goose-neck curved extent 23b, and its upper end 23c extends slightly downwardly to openly terminate in a vertical passage 24 allowing liquid to drip downwardly as indicated by broken line 25 in passage 24.

A clamp block 26 is retained against side 21a of the body 21 to sidewardly clamp the drip tube in recess 22. Note bolts 27 extending from block 26 into body 21 to retain the block to the body. A sensor enclosure 28 extends forwardly of the body, as shown, to form the vertical passage 24, the upper end of which receives the upper end 23c of the drip tube. A lower section 21c of the body 21 forms porting 30 and 31 communicating with the lower end of the drip tube, and a fitting 31 supplies liquid to the porting 30 and 31 to flow to the drip tube. A circuit card 32 is received in a body recess 33, and is electrically connected to pin connector 34 protruding endwise from the body.

A first sleeve 36 is received in a bore 37 in the enclosure 28, and a second sleeve 38 is received in a bore 39 in that enclosure. An infra-red beam generating diode 40 is received in first sleeve 36; and a photodarlington sensor, i.e. photocell 41, is received in second sleeve 38. The infra-red beam axes extending from diode 40 and to the photocell 41 appear at 42 and 43, and generally coincide with the axes of the two sleeves 36 and 38. The angle α between 42 and 43 is less than 90°. Those axes correspond to the beam axes referred to above, in FIGS. 1 and 2.

A window is provided at 46, and retained at 47. Screws 48 hold the retainer in position.

Retention fasteners also are seen at 50 and 51.

Drop 10 may consist of any liquid that will transmit beam 11, as for example transparent oil, water, and other liquids.

I claim:

1. In apparatus for counting a succession of falling liquid drops having teardrop shape, with a downwardly convex lower side, the combination that includes a) a beam provider for providing a beam of electromagnetic radiation to sidewardly pass into the drop at its convex lower side, to be refracted within the drop to pass out of the drop at its convex lower side, b) and a beam detector located to only detect the refracted beam after it has passed sidewardly out of the drop at its convex lower side, c) and wherein the beam provider and detector are located to respectively provide and receive the beam along respective axes located below a drop maximum width zone, said axes forming an acute angle therebetween, whereby the beam remains undetected in the absence of drop passage through the beam.

2. The apparatus of claim 1 wherein, said beam provider is located to direct the beam into the drop below said maximum width zone.

3. The apparatus of claim 1 wherein the beam provider is configured to provide an infra-red beam.

4. The apparatus of claim 2 including a drip supply conduit having a drip outlet located above the line of the beam passing into and out of the drop at predetermined angularity, below said maximum width zone of the falling drip.

5. The apparatus of claim 4 wherein said drip conduit has goose neck configuration.

6. The apparatus of claim 5 including a carrier body carrying said drop conduit, said body defining a slot in which said conduit is received, said body also carrying said beam provider and beam detector below the level of said conduit outlet.

7. The apparatus of claim 6 wherein said body has a downwardly extending drip passage in which the drip may freely fall in a zone defining a vertical axis, said beam provider and detector being located to respectively provide and receive the beam along respective axes directed toward said zone.

8. The apparatus of claim 7 wherein said axes define an angle $\alpha$ therebetween, where $\alpha<90°$.

9. The apparatus of claim 8 wherein said beam provider provides an infra-red beam.

10. The apparatus of claim 1 wherein said axes define an angle $\alpha$ therebetween, where $\alpha<90°$.

11. The apparatus of claim 10 wherein said beam provider provides an infra-red beam.

* * * * *